(12) United States Patent
Mazzarolo (10) Patent No.: US 8,162,865 B2
(45) Date of Patent: Apr. 24, 2012

(54) NECK BRACE

(75) Inventor: Giovanni Mazzarolo, Coste di Maser (IT)

(73) Assignee: Alpinestars Research SRL, Coste di Maser (TV) (IT)

( * ) Notice: Subject to any disclaimer, the term of this patent is extended or adjusted under 35 U.S.C. 154(b) by 277 days.

(21) Appl. No.: 12/529,249

(22) PCT Filed: Mar. 1, 2007

(86) PCT No.: PCT/IT2007/000153
§ 371 (c)(1),
(2), (4) Date: Aug. 31, 2009

(87) PCT Pub. No.: WO2008/105010
PCT Pub. Date: Sep. 4, 2008

(65) Prior Publication Data
US 2010/0056968 A1    Mar. 4, 2010

(51) Int. Cl.
*A61F 5/00* (2006.01)
*A41D 13/00* (2006.01)
(52) U.S. Cl. .............................. 602/18; 2/468
(58) Field of Classification Search ............ 602/19, 602/18, 17, 5, 1; 128/95.1, 97.1; 2/468, 2/455
See application file for complete search history.

(56) References Cited

U.S. PATENT DOCUMENTS

| | | |
|---|---|---|
| 2,820,455 A | 12/1953 | Hall |
| 3,477,425 A | 11/1969 | Grassl |
| 3,495,272 A | 2/1970 | Tempelhof |
| 3,765,412 A | 10/1973 | Ommaya et al. |
| 3,855,631 A | 12/1974 | Ettinger |
| 3,878,561 A | 4/1975 | Winiecki |
| 4,274,161 A | 6/1981 | Littler |
| 4,319,362 A | 3/1982 | Ettinger |
| 4,449,251 A | 5/1984 | Gauthier |
| 4,501,023 A | 2/1985 | Bilberry |
| 4,502,471 A | 3/1985 | Owens |
| 4,821,339 A | 4/1989 | Fair |
| 4,854,306 A | 8/1989 | Pujals |
| 4,996,720 A | 3/1991 | Fair |
| 5,003,968 A | 4/1991 | Mars |
| 5,039,035 A | 8/1991 | Fitzpatrick |

(Continued)

FOREIGN PATENT DOCUMENTS

DE    27 17 712 A1    10/1978
(Continued)

OTHER PUBLICATIONS

"PCT International Search Report dated Nov. 15, 2007 for PCT/IT2007/000153, from which the instant application is based," 2 pgs.

(Continued)

*Primary Examiner* — Patricia Bianco
*Assistant Examiner* — Tarla Patel
(74) *Attorney, Agent, or Firm* — Fredrikson & Byron, P.A.

(57) ABSTRACT

A neck brace (10; 110; 210) having a collar member (12; 212) to be arranged around a wearer's neck, and a rear member (14; 214) extending from, the collar member and to be abutted on the wearer's back. The brace further comprises pivoting means (37, 38, 40, 276a, 278, 280a, 280b, 280c) for pivoting the collar member and the rear member relative to each other about a pivoting axis (X; Y) which, when in use, is substantially parallel to the wearer's shoulders.

20 Claims, 7 Drawing Sheets

U.S. PATENT DOCUMENTS

| | | | |
|---|---|---|---|
| 5,133,084 A | 7/1992 | Martin | |
| 5,230,698 A | 7/1993 | Garth | |
| 5,411,471 A * | 5/1995 | Terrazas | 602/18 |
| 5,437,613 A | 8/1995 | Reggio et al. | |
| 5,517,699 A | 5/1996 | Abraham, II | |
| 5,531,669 A | 7/1996 | Varnau | |
| 5,546,609 A | 8/1996 | Rush, III | |
| 5,590,826 A | 1/1997 | Endo | |
| 6,058,517 A | 5/2000 | Hartunian | |
| 6,067,665 A | 5/2000 | DePalma et al. | |
| 6,494,854 B1 | 12/2002 | Visness et al. | |
| 6,729,643 B1 | 5/2004 | Bassick | |
| 7,041,073 B1 * | 5/2006 | Patron | 602/17 |
| 2004/0167448 A1 | 8/2004 | Heffez | |
| 2007/0106194 A1 * | 5/2007 | Pickering et al. | 602/32 |
| 2010/0121238 A1 | 5/2010 | Mazzarolo | |
| 2010/0235973 A1 | 9/2010 | Mazzarolo | |
| 2010/0251468 A1 | 10/2010 | Mazzarolo | |
| 2010/0263112 A1 | 10/2010 | Mazzarolo | |
| 2011/0004980 A1 | 1/2011 | Leatt et al. | |

FOREIGN PATENT DOCUMENTS

| | | |
|---|---|---|
| DE | 31 36 466 A1 | 4/1983 |
| DE | 295 21 373 U1 | 4/1997 |
| DE | 195 45 299 A1 | 6/1997 |
| DE | 200 06 084 U1 | 8/2001 |
| EP | 0043990 A1 | 1/1982 |
| EP | 0023115 B1 | 12/1985 |
| FR | 2534115 A1 | 4/1984 |
| FR | 2700746 | 7/1994 |
| FR | 2719747 | 11/1995 |
| GB | 2 126 485 A | 3/1984 |
| SL | 9600306 A | 4/1998 |
| WO | 9809545 A1 | 3/1998 |
| WO | 9938401 A1 | 8/1999 |
| WO | 0125088 | 4/2001 |
| WO | 02089620 A1 | 11/2002 |
| WO | 03077793 A2 | 9/2003 |
| WO | 03092561 | 11/2003 |
| WO | 2005051251 A | 6/2005 |
| WO | 2005107658 A | 11/2005 |

OTHER PUBLICATIONS

"PCT International Search Report dated Nov. 15, 2007 for PCT/IT2007/000152," 2 pgs.

English-language Abstract FR2534115 (Nolan Spa).

English-language Abstract FR2700746 (Schegerin).

English-language Abstract FR2719747 (Streiff Motorsport).

* cited by examiner

NECK BRACE

CROSS-REFERENCE TO RELATED APPLICATIONS

This application is a US 371 national stage entry of International Application No. PCT/IT2007/000153, filed Mar. 1, 2007.

BACKGROUND (1) Field of the Invention

The present invention relates to a neck brace used to enhance the protection given by a helmet to the head and neck of a wearer, particularly a rider in a sport activity, e.g. motor racing.

(2) Description of Related Art

It is nowadays compulsory for participant in such sport activities as motor racing to wear helmets in order to protect their heads in the event of an accident.

In order to assure an additional protection to the wearer the use of collars made of resilient material, typically stiff foam, placed between the wearer's upper body and the base of a helmet, has been proposed (see for instance U.S. Pat. No. 6,058,517). The goal is to limit to some degree the movement of the head in case of an impact by reducing the gap in which the helmet can move. However, these collars can be uncomfortable and unduly restrictive to head movements in ordinary situations, e.g. when a motorcyclist wishes to look from side to side while driving.

Other neck braces extend up to the chest and back of the wearer, to maximize the stability of the neck brace. U.S. Pat. No. 6,494,854 discloses a cervical collar made of two rigid parts, a frontal part and a rear part, fastenable together around the neck. WO 2005 051 252 discloses a neck brace with a collar member and a back member. The collar member is hingedly divaricable in two halves which open laterally and let insert the neck therebetween, while the back member is fixed to one of the two halves.

Neck braces of this type have the major drawback that they are difficult to adapt to one's body. Furthermore these braces are overly restrictive and do not easily co-operate with other items of protective clothing that the user may have to wear to partake in their sport. Also, they are unsuitable to be fitted on a rider's suit.

BRIEF SUMMARY OF THE INVENTION

The main object of the present invention is to provide a neck brace capable to overcome some of the above-mentioned drawbacks.

This object is obtained by a neck brace having a collar member to be arranged around a wearer's neck, and a rear (back) member projecting from the collar member and adapted to rest on the wearer's back, characterized by comprising pivoting means for pivoting the collar member and the rear member.

Since the pivoting means allow the angle between the collar member and the back member to be changed at will, the profile of the neck brace can be changed as well, thereby being able to adapt its shape continuously and "sit" on the rider's shoulders easily.

According to a preferred embodiment of the invention, an aerodynamic hump is placed on the rear member to block the mutual movement between the collar and the rear member and to fix the angle thereof.

According to another preferred embodiment of the invention, the rear member . . .

A neck brace (10; 110; 210) having
a collar member (12; 212) to be arranged around a wearer's neck, and
a rear member (14; 214) extending from the collar member and to be abutted on the wearer's back,
characterized by comprising pivoting means (37, 38, 40; 276a, 276b, 278, 280a, 280b, 280c) for pivoting the collar member and the rear member relative to each other about a pivoting axis (X; Y) which, when in use, is substantially parallel to the wearer's shoulders.

2. Neck brace (10; 110; 210) according to Claim 1, wherein the pivoting means are releasable means, such that the collar member and the rear member may be detached.

3. Neck brace (10; 110; 210) according to Claim 1 or 2, comprising limiting means (45; 48; 272a, 272b) for limiting the amplitude of the angle between the collar member and the rear member.

BRIEF DESCRIPTION OF THE SEVERAL VIEWS OF THE DRAWINGS

Further features and advantages of the invention will better appear from the following description of some embodiments thereof, with reference to the accompanying drawings, in which.

DETAILED DESCRIPTION OF THE INVENTION

In the following, references with suffix "a" and "b" are to be understood to be mean equal or corresponding parts in the neck-brace, since the same or similar components are designed with the same numerals, which for sake of conciseness will not be described more than once.

Figure 1:
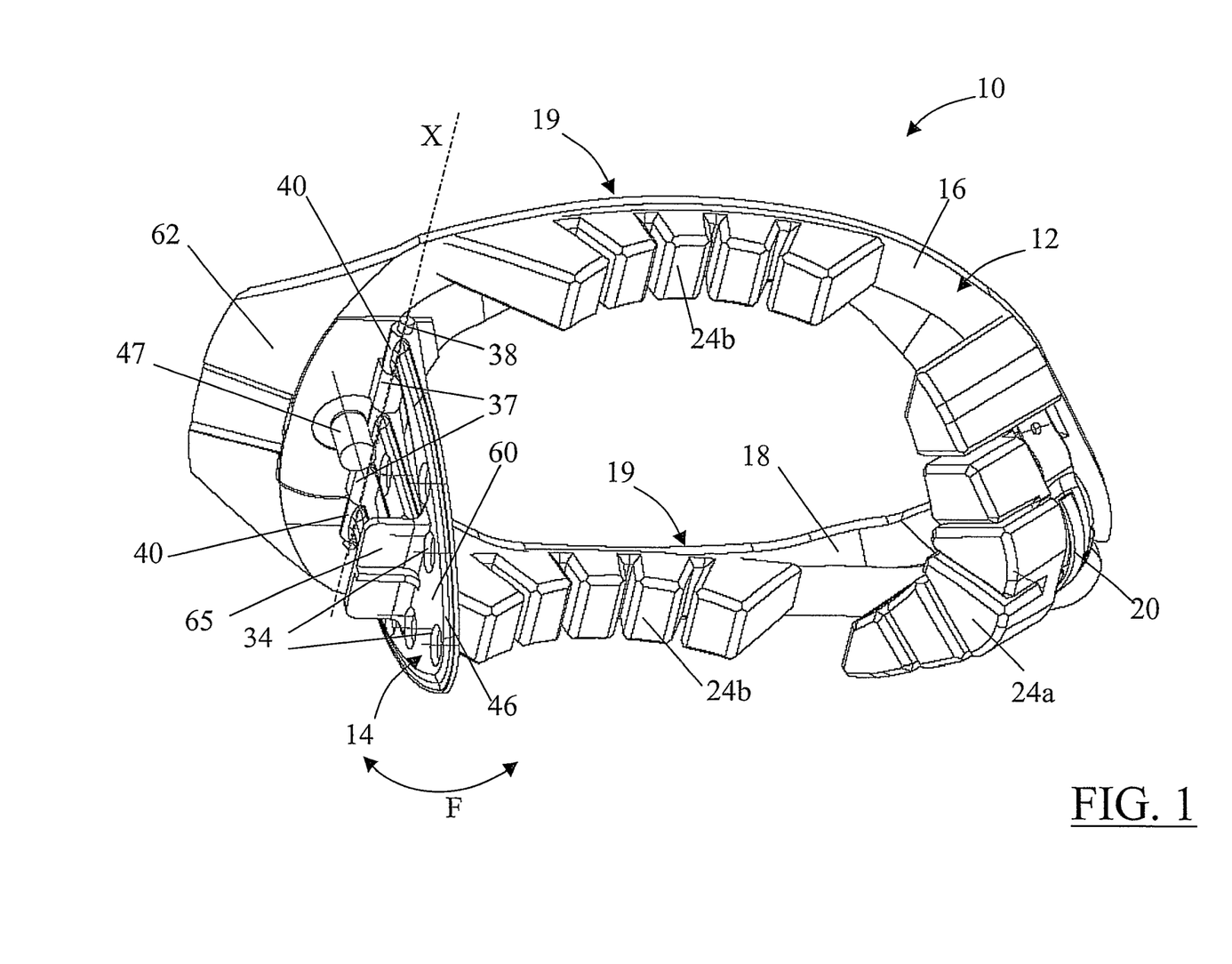
FIG. 1 shows a three-dimensional view of a neck brace according to the invention.

With reference first to FIG. 1, a neck brace, generally designed with reference 10, has a collar member 12, which, in use, extends around a wearer's neck, and a rear member 14, which, in use, rests upon the wearer's back.

The collar member 12 comprises two semi-circular halves 16, 18 which are frontally (i.e. at the wearer's chin) connected through closure means, in the example a releasable buckle 20, and, in the back (i.e. at a wearer's nape), jointed by pivoting means, in the example a hinge 22.

By releasing the buckle 20, the two halves 16, 18, due to the hinge 22, can rotate outward, thereby opening the collar member 12 and making it possible for a wearer to insert the neck.

The two halves 16, 18 have an upper surface 19, which, in use, can abut against the lower surface of a helmet (shown in broken lines in FIG. 2) and toothed projections 24a, b which extend downwards from the collar member 12. These projections 24a, b are made of a rigid and undeformable material, e.g. plastic materials and the like, and are designed to rest, in use, respectively, on wearer's shoulders and upper chest portion.

The rear member 14 has a semi-elliptical base-plate 60 (made of plastics or metal material), with a plurality of openings 34 (only few indicated) which can cooperate with a plurality of studs provided onto the rider's garment to fix it thereupon.

The rear member 14 further comprise cylindrical bored terminations 40 which rotatably cooperate with adjacent bored flanges 37 integral with the collar member 12 by means of a longitudinal pin 38 inserted therein. In this way the rear and collar members 12, 14 can pivot relatively to each other about an axis X which, when the brace 10 is in use, is substantially parallel to the wearer's shoulders (see also direction F of mutual rotation in FIG. 1). It is to be noted that pivoting means in the form of an extractable pin form also releasable means: therefore the collar member 12 and the rear member 14 may be easily detached only by sliding out the pin 38.

When using the neck brace 10, the host garment may not have an aerodynamic hump ready attached. Thanks to the invention a hump 45 (see FIG. 2) can be attached to the rear member 14, in particular to the base-plate 60, on which the aerodynamic hump 45 can be accommodated abutting with a rear flange 62 in the collar member 12. The opposition of the flange 62 to the hump 45 (when mounted) allows fixing the relative angle, and preventing a divarication between the collar member 12 and the rear member 14, just for opposition of parts. On the rear flange 62 there are provided engaging means for retaining the hump 45 in the form of a stud 47, arranged to engage the hump 45 before that, during assembly, it is rotated downwards onto a Velcro® pad 46 attached on the surface of the base-plate 60. More studs 47 or similar pins can be provided for better fitting and security. A proper design, for instance by introducing some play between the stud 47 or the flange 62 and the hump 45, may allow the collar member 12 to be bent towards the chest but not in the opposite verse.

Figure 2:
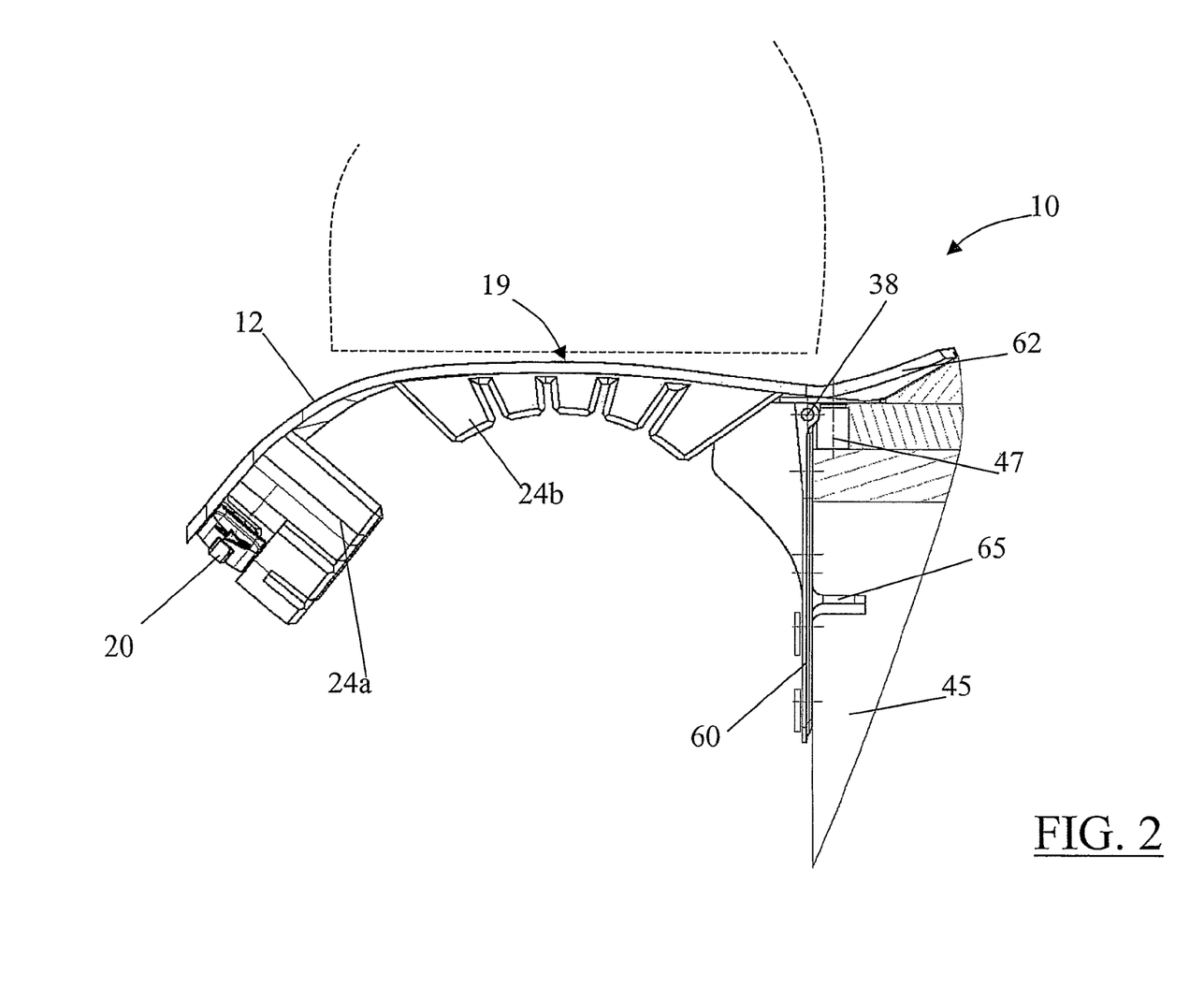
FIG. 2 shows a side view with cut-out portions of the neck brace of FIG. 1.

In the event that the head is impacted such that it tilts backwards, the stud 47 pushes the hump 45 against the Velcro® pad 46 causing the hump 45 not to slide downwards during the impact.

To further assure a better safety, the base-plate 60 is provided with further engaging means for retaining the hump 45 in the form of projections 65 able to support and/or fix the hump 45. As for the stud 47, the projections 65 are shaped to engage complementary cavities in the hump 45.

The base-plate 60 is attached to the back of the host garment by means of the openings 34 or other fastening means. The host garment may not have a hump ready attached, but a hump can be attached to the same fixings when the brace is not used. This is a great advantage.

The collar member 12 can then be attached by inserting the pin 38 through the pivot point. At this point the collar member 12 and the rear member 14 can relatively rotate around the axis X.

Opening the buckle 20 opens the two semi-circular halves 16, 18, of which one can be rotated outward because of the hinge 22. The garment is then put on normally and at the end the brace 10 is closed, the buckle 20 fastened, and studs on the front are clipped to the garment. The projections 24a, b that sit on the shoulders are attached with Velcro and can be moved forward or backwards as required such that they centred over the riders shoulders. The upper surface 19 then limits the overall movement of the head by interfering with the base of the helmet.

One of the advantages of having pivoting means as those of the invention is that the profile (angle) of the brace 10 can be changed at will by changing the shape of the hump 45. The behaviour of the brace 10 under impact can also be changed by altering the material type of the top portion of the hump 45, the one abutting with the flange 62. This is better illustrated in the cutaway section of FIG. 2. The hump 45 can be mainly made from a light, rigid foam such as High Density Polystyrene, with some embedded plastic ribs.

It is to be noted that, if the hump 45 has a soft upper portion, it may also constitute resilient means such that the collar member 12 and the rear member 14 can elastically oscillate around an idle position.

Figure 3:
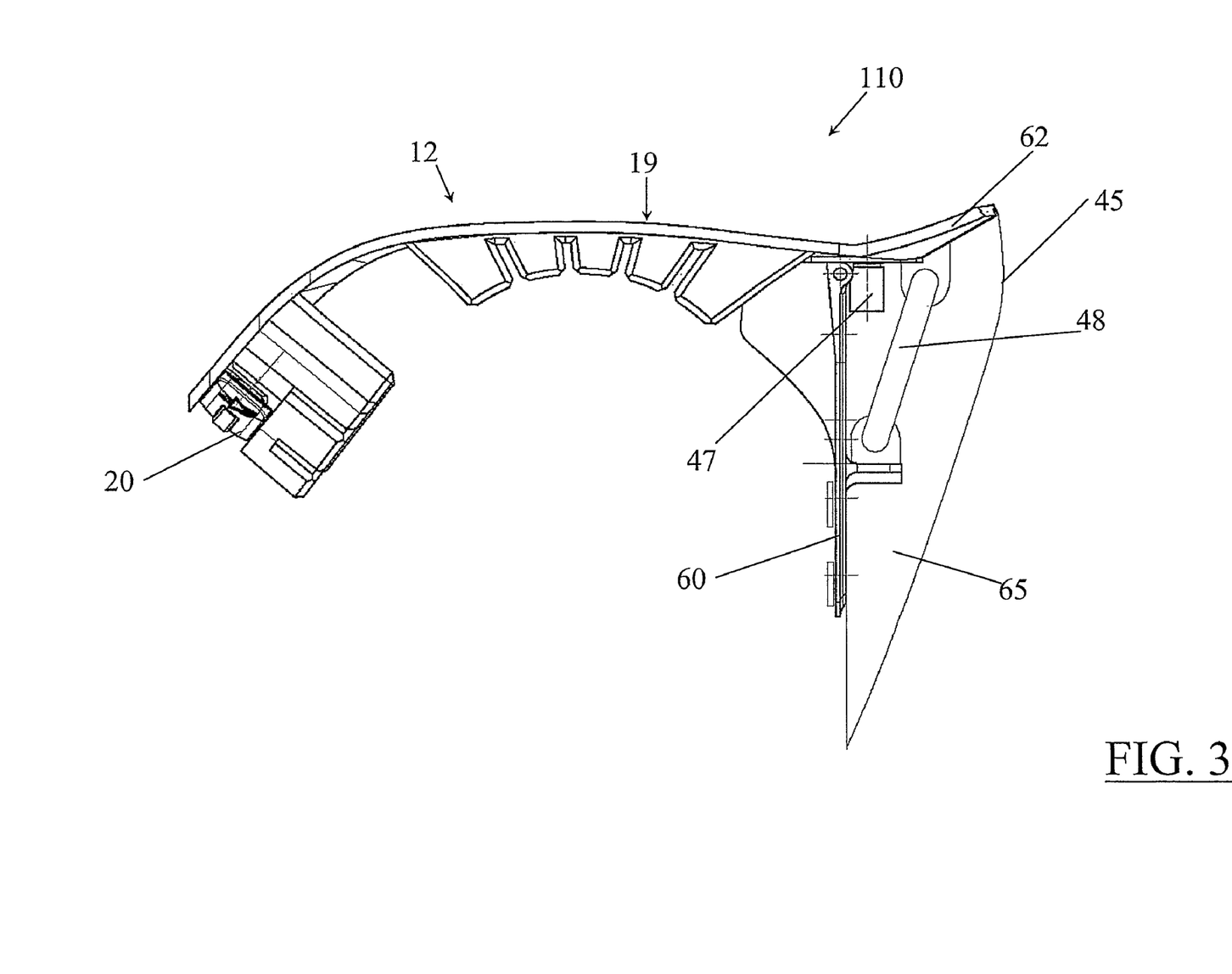
FIG. 3 shows another embodiment in a side view with cut-out portions of a neck brace according to the present invention.

In an alternative embodiment 110 illustrated in FIG. 3, a mechanical arrangement between the collar member and the rear member is used to limit the divarication thereof.

A rigid elongated element 48 is connected between the flange 62 and the base-plate 60 and connected thereto in a connecting-rod-like manner in order to block their mutual position. The elongated member 48 may be adjustable in length, thereby allowing the adjustment of the divarication between the collar member 12 and the rear member 14.

Resilient means (springs or a damping unit to help decelerate the head) may be interposed in the elongated member 48 or its connecting points, such that the collar member 12 and the rear member 14 can elastically oscillate around an idle position. As this arrangement is not particularly aerodynamic, a soft outer shell could be used to conceal the mechanism or a hump can be adapted to fit thereon.

Figure 4:
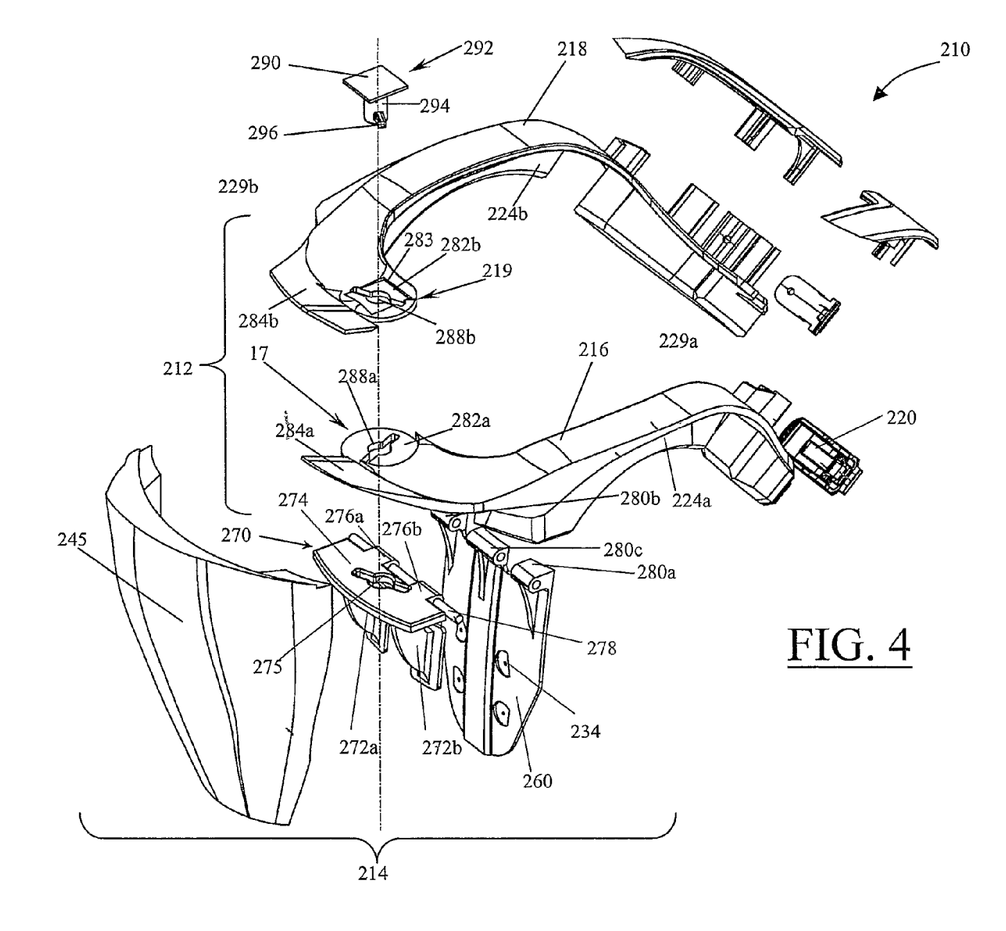
FIG. 4 shows an exploded view of another embodiment of the neck-brace according to the invention.

With reference first to FIG. 4, another neck brace according to the invention, generally indicated with reference 210, has a collar member 212, which, in use, extends around a wearer's neck, and a rear member 214, which, in use, rests upon the wearer's back.

The collar member 212 comprises two semi-circular halves 216, 218 which are frontally (i.e. at a wearer's chin) connected through closure means, e.g. a releasable buckle 220. The circular halves 216, 218 at the wearer's nape are jointed by releasable fastening means to each other and to the rear member 214, as more particularly described below.

The two halves 216, 218 have an upper surface 229a, b, which, in use, can abut against the lower surface of a helmet (not shown) and padded projections 224a, b which extend downwards from the collar member 212 at the shoulder and on the upper chest of the device. These projections 224a, b can be made of rigid material which would deform slightly under impact, e.g. high density expanded foams and the like, or softer materials, and are designed to rest, in use, on the wearer's shoulders and upper chest.

The two halves 216, 218 have a particular configuration in their rear section. Their rear ends 217, 219 are curved towards each other, rounded and end with a circular planar zone 282a, b rimmed with a lip 284a, b which projects outwards from the collar member 212. In the middle of each planar zone 282a, b there is a rectangular transverse slot 288a, b with a circular enlargement in the centre thereof. The planar zone 282b has a little deep squared (or generally polygonal) recess 283 on whose diagonal the slot 288b is obtained. The plant of the recess 283 corresponds to that of a plain head 290 comprised in a separated locking key 292 having a cylindrical body 294 with transverse projecting pins 296. The length of the pin 296 is the same as that of the slots 288a, b. The two rounded ends 217, 219 are shaped to be superimposed over each other and to be rotatable over one another. This thanks to the receiving planar zone 282a, which is the lower one and is slightly recessed to accommodate snugly the upper zone 282b. When two rounded ends 217, 219 are mounted superimposed the circular enlargements in the centre of the slots 288a, b line up. However, it is to be noted that, since the orientation of the slots 288a, b is not the same, namely they form different angles with respect to the longitudinal axes of the relative half part 216, 218 of the collar member 212, the slots 288a, b can line up only in a given open angular position of the halves 216, 218.

It is desired that when the halves 216, 218 are parallel (closed configuration for the collar member 212) the slots 288a, b do not line up, while they must line up when the halves 216, 218 are divaricated by a given amount (open configuration for the collar member 212). How to use and wear the collar member 212 will be given hereunder.

The rear member 214 has a semi-elliptical base-plate 260 (made of plastic or metal material of any suitable type), with a plurality of openings 234 (only one indicated) which can cooperate with a plurality of studs (or viceversa) provided onto the rider's garment to fix it thereupon. Velcro may be used as well for the fixing.

To the base-plate 260, on which an aerodynamic hump 245 can be accommodated, there is hinged a support member 270 composed by two arched legs 272a, b and an upper plate 274. The legs 272a, b protrude from underneath the plate 274 and abut on the base-plate 260, while the upper plate 274 has two cylindrical bushes 276a, b provided on a border which are passed through by a pin 278. See the circle in broken lines of FIG. 5 for a bottom view of the support 270. The pin 278 also engages three bushes 280a, b, c on the upper border of the base-plate 260, thereby hinging the latter with the support member 270 about a pivoting axis Y which, when in use, is substantially parallel to the wearer's shoulders.

Figure 8:
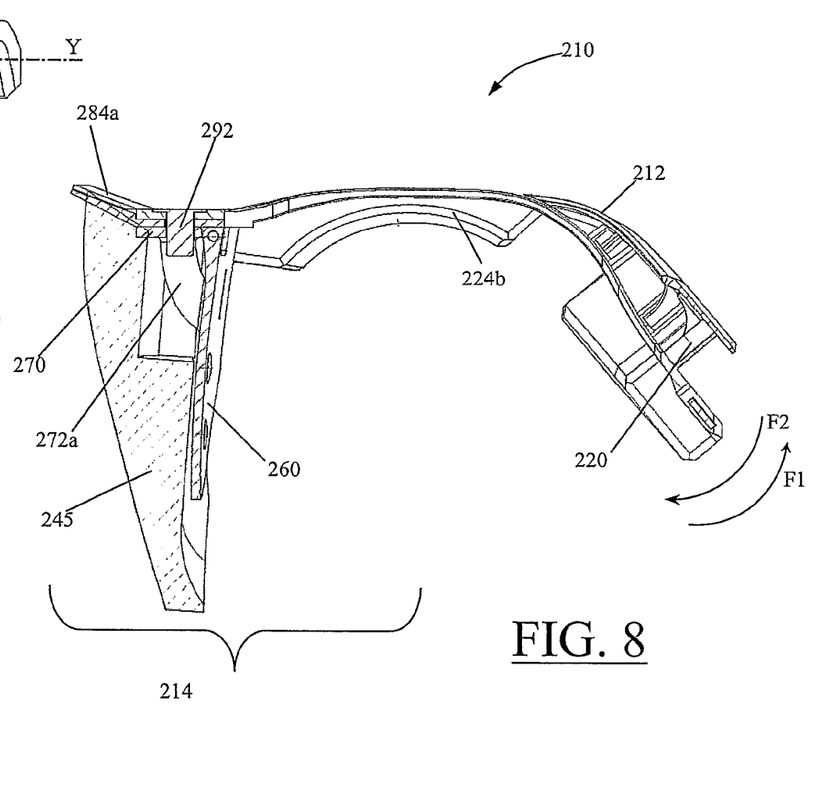
FIG. 8 shows a cross-sectional view of the assembled neck-brace in FIG. 4 along the section-plane A-A.

It is to be noted that the legs 272a, b limit the down-to-up movement of the collar member 212 relative to the rear member 214 (see arrow F1 in FIG. 8), while allowing a slight up-to-down movement (see arrow F2 in FIG. 8). One or more legs 272a, b or similar protrusions, even with different shape, may be used. The same result may be obtained by joining the collar member 212 and the support member 270 in a single piece.

Figure 5:
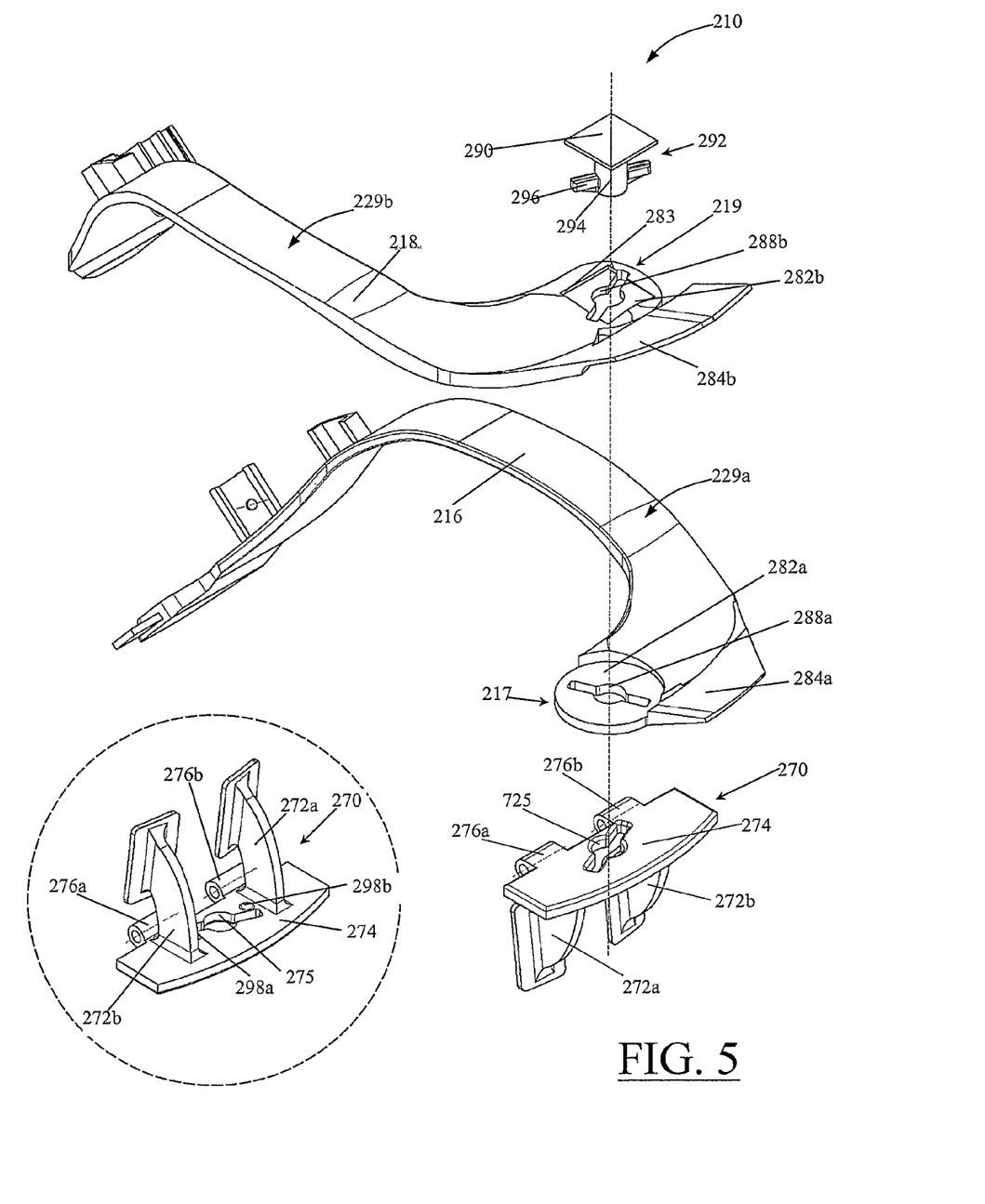
FIG. 5 shows a further exploded view of the principal parts of the neck-brace in FIG. 4.
Figure 6:
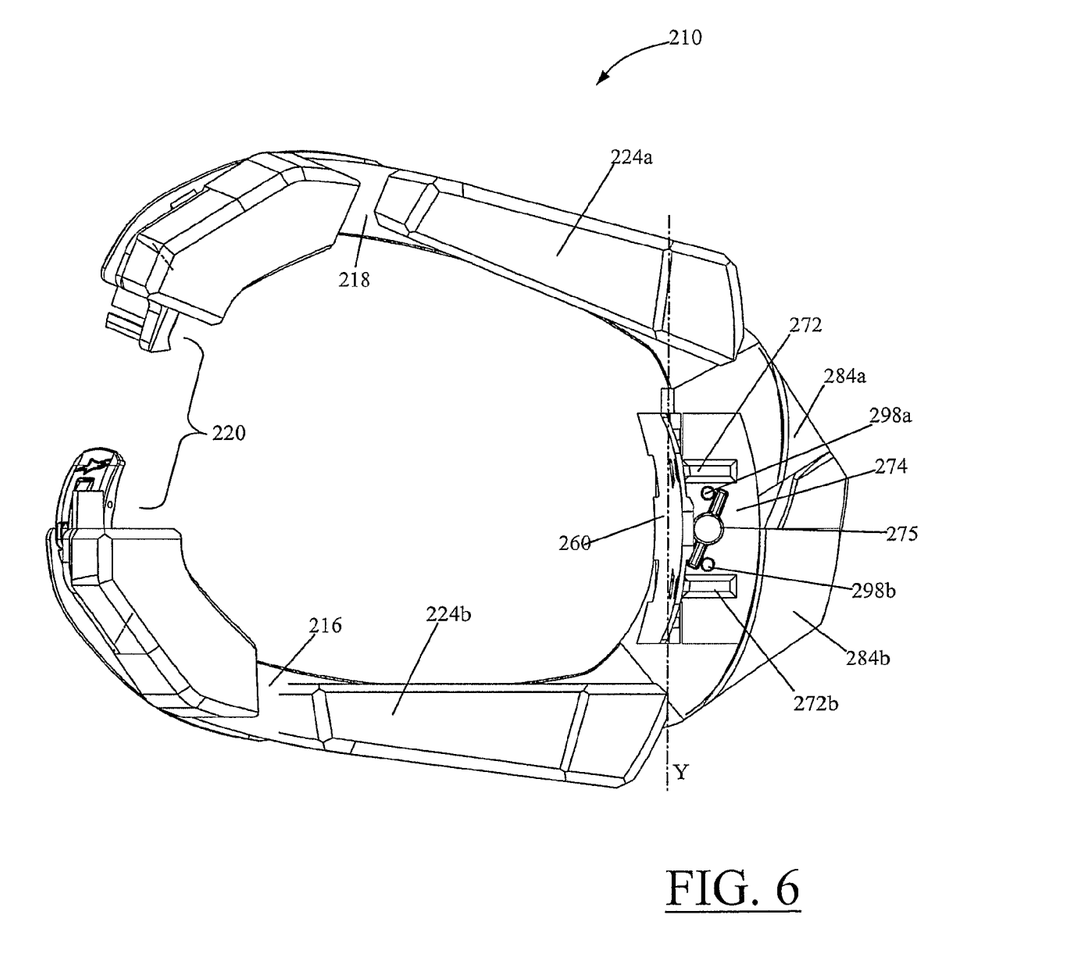
FIG. 6 shows a bottom view of the assembled neck-brace in FIG. 4.
Figure 7:
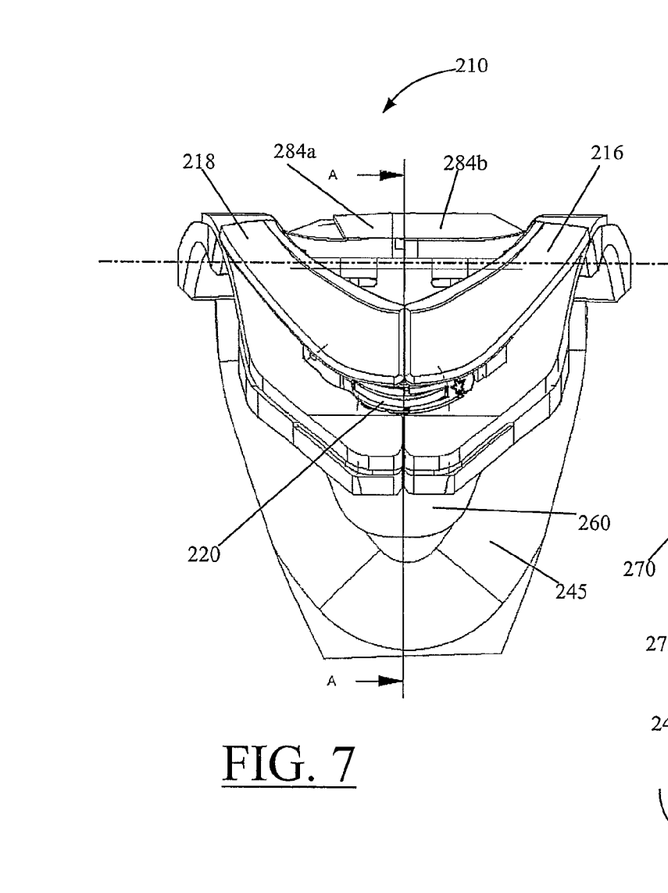
FIG. 7 shows a front view of the assembled neck-brace in FIG. 4.

The upper plate 274 has a transverse slot 275, with dimensions equal to the slots 288a, b, but with different orientation with respect to them when the halves 216, 218 are parallel. Beside the slot 275, on the surface of the upper plate 274 facing the legs 272a, b, there are two lenticular dimples 298a, b.

The neck brace 10 can be worn as follows.

The plate 260 is attached to the rider's suit using stud fasteners and Velcro, and the support member 270 is hinged to the plate 260 using the pin 278. By abutting with the legs 272a, b against the edge of the plate 260 the support member 270 defines the amount of rearward freedom of the collar member 212 and it should be noted that, by interchanging the support piece 270 with another one of different dimensions for the legs 272a, 272b, the angle (between the members 212 and 214) of the brace 210 can be adjusted. Then for aerodynamic and styling purposes the padded hump 245 shape is attached to the back of the plate 260 (i.e. with means as described above).

The locking key 292 is inserted in the slot 288b and its head 290 fitted in the complementary recess 283, thereby making it integrally rotatable with the half 218.

The two halves 216, 218 are then divaricated and superimposed in order to line up the slots 288a, 288b. Then the pin 296 of the locking key 292 is inserted into the slot 288a of the half 216 as well.

To don the collar member 212 the user then slides it over the neck from back to front. Without closing the halves 216, 218 the user then moves the collar member 212 down at the rear to engage the pin 296 in the slot 275 on the support element 270. At this point the user then rotates the halves 216, 218 to bring them near the neck, and fastens them with the frontal buckle 220. This single action causes the locking key 292, and hence the pin 296, to rotate on the underside of the support member 270. Thus the pin 296 jumps over the dimples 298a, b and stays secured on the other side thereof. This way the halves 216, 218 are coupled to the support member 270 (and hence to the garment of the rider) by means of the pin 296, which after rotation cannot escape form the slot 275.

To remove the collar member 212 the user opens the buckle 220, and separates the halves 216, 218. This will rotate the locking key 292 such that the pin 96 lines up with the slot 275, and the halves 216, 218 will be released therefrom. Once free from the support member 270, the halves 216, 218 may continue to be separated such that the pin 296 lines up with the slot 288a and the two halves 216, 218 can come apart. This reduces the overall size of the brace 210 and makes it easier for storage and transportation.

All the features disclosed in one embodiment can be adapted and integrated in the other embodiment. Also, some described secondary features may be missing in an embodiment, being only a choice of final design.

The invention claimed is:

1. A neck brace having a collar member to be arranged around a wearer's neck, and a rear member extending from the collar member and to be abutted on the wearer's back, characterized by comprising pivoting means for pivoting the collar member and the rear member relative to each other about a pivoting axis which, when in use, is substantially parallel to the wearer's shoulders, wherein the pivoting means further serve as releasable means by which the collar member and the rear member are detachable from each other.

2. The neck brace of claim 1 further comprising limiting means for limiting the amplitude of the angle between the collar member and the rear member.

3. The neck brace of claim 1 wherein the collar member comprises a base-plate able to be accommodated on the back of a rider's suit.

4. The neck brace of claim 3 wherein the base-plate comprises fastening means to fasten the base-plate to the back of a rider's suit.

5. The neck brace of claim 4 wherein said fastening means comprise openings and/or studs adapted to cooperate with corresponding parts provided in the back of a rider's suit.

6. The neck brace of claim 3 wherein the base-plate is adapted to accommodate an aerodynamic hump thereon.

7. The neck brace of claim 6 wherein on the base-plate there are provided engaging means for engaging the hump in place and fix it.

8. The neck brace of claim 7 wherein said engaging means for retaining the hump comprise one or more projections from the base-plate able to support and/or fix the hump.

9. The neck brace of claim 6 wherein the collar member comprises a rear flange against which said hump when mounted may abut, thereby setting the amplitude of the relative angle between the collar member and the rear member.

10. The neck brace of claim 9 wherein on the rear flange there are provided engaging means for retaining the hump.

11. The neck brace of claim 10 wherein said engaging means for retaining the hump comprise one or more pins projecting towards the base-plate.

12. The neck brace of claim 1 further comprising a mechanical arrangement between the collar member and the rear member to limit the amplitude of divarication thereof.

13. The neck brace of claim 12 wherein said mechanical arrangement comprises an elongated rigid member placed between the collar member and the rear member and connected thereto in order to set their mutual position.

14. The neck brace of claim 13 wherein said elongated rigid member is adjustable in length, thereby allowing the adjustment of the divarication between the collar member and the rear member.

15. The neck brace of claim 12 wherein said mechanical arrangement comprises resilient means such that the collar member and the rear member can elastically pivot around an idle position.

16. The neck brace of claim 1 wherein said pivoting means comprise bored terminations provided on the rear member which rotatably cooperate with bored flanges integral with the collar member by means of a longitudinal pin inserted therein.

17. The neck brace of claim 1 wherein the collar member is provided with one or more arched protrusions being able to abut against the rear member in order to limit the amplitude of the relative angle between the collar member and the rear member.

18. The neck brace of claim 17 wherein the collar member is fixed to a support member hinged to the rear member.

19. The neck brace of claim 18 wherein the one or more arched protrusions are provided in the support member.

20. The neck brace of claim 1 wherein removal of the collar from the wearer prompts a condition by which the collar member is detachable from the rear member via the releasable means.

* * * * *